United States Patent
Okada

(10) Patent No.: US 6,376,719 B1
(45) Date of Patent: Apr. 23, 2002

(54) PROCESS FOR THE PREPARATION OF ALKALINE EARTH METAL SALTS OF β-DIKETO COMPOUNDS

(75) Inventor: Masayuki Okada, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/508,459

(22) PCT Filed: Jul. 6, 1999

(86) PCT No.: PCT/JP99/03653

§ 371 Date: Mar. 10, 2000

§ 102(e) Date: Mar. 10, 2000

(87) PCT Pub. No.: WO00/02838

PCT Pub. Date: Jan. 20, 2000

(30) Foreign Application Priority Data

Jul. 10, 1998 (JP) ............................. 10-196247

(51) Int. Cl.$^7$ ................ C07C 49/12; C07C 45/00; C07C 49/00; C07C 49/04; C07C 69/66; C07C 69/72

(52) U.S. Cl. .............. 568/412; 568/303; 568/350; 568/382; 568/383; 560/174; 560/178

(58) Field of Search ............................... 568/303, 350, 568/382, 383, 412; 560/174, 178

(56) References Cited

FOREIGN PATENT DOCUMENTS

| DE | 1960320 C2 | 9/1997 |
|---|---|---|
| JP | A52-136131 | 11/1977 |
| JP | A59-139339 | 8/1984 |
| JP | B2-6024777 | 6/1985 |
| JP | A3-2138 | 1/1991 |
| JP | A4-134044 | 5/1992 |
| JP | A5-9608 | 1/1993 |
| JP | A5-239066 | 9/1993 |
| JP | A5-239067 | 9/1993 |
| JP | A5-255855 | 10/1993 |
| WO | 97/34859 | * 9/1997 ........... C07C/45/77 |

OTHER PUBLICATIONS

Zn. Neorg. Khim, (1990), 35(11), 2776–80.

* cited by examiner

*Primary Examiner*—Samuel Barts
*Assistant Examiner*—Elvis O. Prize
(74) *Attorney, Agent, or Firm*—Birch, Stewart, Kolasch & Birch, LLP

(57) ABSTRACT

An alkaline earth metal salt of β-diketo compound is produced using 1 mol of a powdery alkaline earth metal compound and 2.04 mol or more of an aliphatic β-diketo compound. The reaction may be carried out while supplying both components to a reactor continuously or intermittently, or may be carried out by adding one component to the other continuously or intermittently. The highest temperature during the reaction may be at 50° C. or higher. The reaction mixture may be aged, and then dried at a temperature of at 100 to 180° C. in an atmosphere of an inert gas. The alkaline earth metal compound may be calcium hydroxide, magnesium hydroxide, or barium hydroxide. The aliphatic β-diketo compound may be represented by the following formula, particularly an acetoacetic acid ester or acetylacetone.

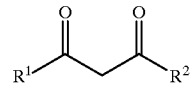

(1)

According to the production method as mentioned above, highly stable alkaline earth metal salts of β-diketo compounds of high quality can be produced.

8 Claims, No Drawings

PROCESS FOR THE PREPARATION OF ALKALINE EARTH METAL SALTS OF β-DIKETO COMPOUNDS

TECHNICAL FIELD

This is the National phase Application of PCT/J199/03653, filed Jul. 6, 1999.

The present invention relates to an alkaline earth metal salt of a β-diketo compound which is used as an auxiliary for resin molding, and to a method for producing the same.

BACKGROUND ART

Alkaline earth metal salts of β-diketo compounds (hereinafter, referred to as β-diketo compound salts or salts of β-diketo compounds) are utilized as auxiliaries for resin molding, particularly, as nonpoisonous or nontoxic stabilizers for vinyl chloride resin molding.

Various methods for producing the β-diketo compound salt are known. For example, Zh. Neorg. Khim. (1990), 35(11), 2776–80 discloses a method for producing a β-diketo compound salt by a reaction between acetylacetone and calcium chloride or calcium nitrate. However, the method is disadvantageous in terms of quality, because it is necessary to remove impurities such as a chloride and a nitrate (or anitric acid salt) contaminating the resulting β-diketo compound salt (acetylacetonato).

Japanese Patent Publication No. 24777/1985 (JP-B-60-24777) describes a method for producing a β-diketo compound salt by adding an alkaline earth metal hydroxide to a β-diketo compound (e.g., acetylacetone) in a ratio of 1 mol of the former to the equivalent (2 mol) of the latter. However, according to this method, the viscosity rises in the latter half of the reaction, increasing the load on the power that the mixer requires. For such reasons, the method involves an expensive reactor, and thus is industrially disadvantageous. Further, the β-diketo compound salt thus obtained is not suitable for use as a stabilizer, because the salt contains about 6 to 7% by weight of moisture (corresponding to one molecule of water of crystallization). For example, when a stabilizer containing water of crystallization is used in molding a vinyl chloride resin, bubbling due to water vapor remarkably deteriorates the strength and clarity (transparency) of the vinyl chloride resin. Furthermore, since the stability of the β-diketo compound salt produced in accordance with the process of the literature is low, the salt cannot be preserved for long periods of time. For example, when a calcium salt of acetylacetone produced according to the method is dried to a water (moisture) content of 1% by weight or less, the purity of the salt is remarkably lowered from 97% by weight to 86% by weight in a month.

Furthermore, German Patent DE96-19610320 describes a method for producing a β-diketo compound salt by adding a β-diketo compound (e.g., acetylacetone) to an alkaline earth methyl hydroxide in the absence of a solvent using 1 mol of the latter and the equivalent (2 mols) of the former. In the method described in this literature, the β-diketo compound is added to the alkaline earth metal hydroxide and reacted at 40° C. or lower, thus preventing the viscosity of the reaction mixture from becoming too high and making it possible to react the reaction mixture in the form of particles or powder. However, according to the method of the literature, the β-diketo compound needs to be added slowly in order to prevent the viscosity from becoming too high. Therefore, it takes time to complete the reaction, the conversion is low (for example, about 94% when hydrated lime is used), and the resulting β-diketo compound salt is of lower purity.

Accordingly, it is an object of the present invention to provide highly stable β-diketo compound salts of higher quality and a method for producing the same.

It is another object of the present invention to provide, regardless of a reactant being reacted in powdery form (or in the form of particles), a method whereby β-diketo compound salts of high purity can industrially advantageously be produced at high conversions without an increase in viscosity.

It is still another object of the present invention to provide a method for effectively producing β-diketo compound salts within a short period of time without lowering the conversion and purity.

DISCLOSURE OF INVENTION

The inventors of the present invention have found that, when an alkaline earth metal hydroxide such as calcium hydroxide remains unreacted, the purity of a β-diketo compound salt is remarkably decreased during its preservation probably because of the condensation of an acetylacetone unit of the β-diketo compound salt. Based on such knowledge, the inventors did intensive research to achieve the above objects, and finally found that, when an aliphatic β-diketo compound is used in an excess amount relative to the amount of an alkaline earth metal compound, the resulting β-diketo compound salt is of high purity and highly stable. The present invention was accomplished based on the above findings.

In summary, the present invention is a method for producing an alkaline earth metal salt of a β-diketo compound from a powdery alkaline earth metal compound and an aliphatic β-diketo compound, wherein 2.04 mol or more of the aliphatic β-diketo compound is used relative to 1 mol of the alkaline earth metal compound. The reaction may be carried out while supplying the alkaline earth metal compound and the aliphatic β-diketo compound continuously or intermittently, or by adding one component to the other continuously or intermittently. The total amount of each component used need only be within the above range, and the amount of each component in a reaction stage or a supply stage need not be within the above range. Furthermore, the highest temperature throughout the reaction may be 50° C. or higher, and a drying operation may be conducted at 100 to 180° C. in an atmosphere of an inert gas. The alkaline earth metal compound may be calcium hydroxide, magnesium hydroxide, or barium hydroxide. Moreover, the aliphatic β-diketo compound may be represented by the following formula (1):

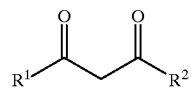

(1)

wherein $R^1$ and $R^2$ are same or different, each representing hydrogen atom, a $C_{1-6}$ alkyl group, or a $C_{1-10}$ alkoxy group, or may be an acetoacetic acid $C_{1-4}$ alkyl ester or acetylacetone.

Furthermore, the alkaline earth metal salt of the β-diketo compound of the present invention is produced according to the method as described above. The alkaline earth metal salt of a β-diketo compound contains 1% by weight or less of water (moisture) and has a purity of not less than 98% by weight.

BEST MODE FOR CARRYING OUT THE INVENTION

[Alkaline earth metal compound]

As the alkaline earth metal compound, there may be exemplified hydroxides of alkaline earth metals (for example, magnesium hydroxide, calcium hydroxide, and barium hydroxide). These alkaline earth metal compounds may be used singly or as a combination of two or more species.

The alkaline earth metal compound may be used in the form of particles or in powdery form. Those commercially available for industrial use may be used as they are. The mean particle size of the alkaline earth metal compound is about 0.1 to 300 μm, preferably about 0.1 to 150 μm.

Further, it is preferred that the alkaline earth metal compound contains little or no impurities (e.g., silica, alumina, alkaline earth metal carbonates). The amount of impurities is, for example, 2% by weight or less, preferably 1% by weight or less, more preferably 0.5% by weight or less.

[Aliphatic β-diketo compound]

As the aliphatic β-diketo compound, compounds of the formula (1) may be used. In the formula (1), $R^1$ and $R^2$ may be same or different, each representing a hydrogen atom, a $C_{1-6}$ alkyl group (for example, $C_{1-4}$ alkyl groups such as methyl and ethyl groups), or a $C_{1-10}$ alkoxy group (for example, $C_{1-6}$ alkoxy groups such as methoxy, ethoxy, propoxy and butoxy groups). For example, there are exemplified compounds having a 2,4-alkanedione or acetoacetic acid ester structure.

Preferred aliphatic β-diketo compounds are compounds represented by the formula (1) wherein $R^1$ is a $C_{1-4}$ alkyl group (e.g., methyl group, ethyl group) and $R^2$ is a $C_{1-4}$ alkyl group (e.g., methyl group, ethyl group) or $C_{1-6}$ alkoxy group (e.g., methoxy, ethoxy, propoxy and butoxy groups). Even when both $R^1$ and $R^2$ are $C_{1-4}$ alkyl groups, they may be the same or different $C_{1-4}$ alkyl groups. Included among the particularly preferred aliphatic β-diketo compounds are acetylacetone and acetoacetic acid $C_{1-4}$ alkyl esters (e.g., methyl acetoacetate, ethyl acetoacetate).

Commercially available aliphatic β-diketo compounds for industrial use may be employed as they are.

According to the present invention, since an excess of an aliphatic β-diketo compound is used relative to the amount of an alkaline earth metal compound, there is produced a highly stable β-diketo compound salt of high purity regardless of reaction method. In other words, according to the present invention, the aliphatic β-diketo compound is used in an amount of not less than 2.04 mol, for example, about 2.04 to 5 mol (for example, about 2.05 to 4.5 mol), preferably about 2.1 to 4 mol (for example, about 2.1 to 3 mol), more preferably about 2.2 to 2.8 mol (for example, about 2.2 to 2.6 mol), relative to 1 mol of the alkaline earth metal compound. The amount of the remaining alkaline earth metal compound is reduced by merely using the aliphatic β-diketo compound in an amount slightly exceeding 2 mol. However, when the aliphatic β-diketo compound is used too much, the viscosity of the reaction mixture becomes high (i.e., like a viscous paste) at near the end of the reaction, and therefore it is difficult to stir the mixture.

[Reaction]

According to the present invention, salts of β-diketo compounds can be produced by reacting the β-diketo compound with the alkaline earth metal compound while maintaining the flowability of the powder (or particles).

The reaction between the alkaline earth metal compound and the β-diketo compound can be carried out by supplying the alkaline earth metal compound and the β-diketo compound to a reactor continuously or intermittently. For example, the reaction between the alkaline earth metal compound and the β-diketo compound can be performed by supplying these compounds to a reactor capable of mixing (apparatuses for kneading or blending powders, such as kneaders, channel-type dryers, ribbon blenders) via a feeder or supplying machine (e.g., metering supply machine).

When continuously or intermittently supplying the alkaline earth metal compound and the aliphatic β-diketo compound to the reactor, each component may be supplied to the reactor in the aforementioned proportion, or each component may be supplied such that the proportion of the component at the end of the supply (the total of each component used) is within the range mentioned above.

Alternatively, the reaction may be effected by adding, between the alkaline earth metal compound and the aliphatic β-diketo compound, one component to the other. Though possible to provide highly stable β-diketo compound salts of high purity by adding the β-diketo compound to the alkaline earth metal compound continuously or intermittently, the reaction mixture may sometimes grow viscous in the latter half of the reaction. Accordingly, it is advantageous to carry out the reaction by adding the aliphatic β-diketo compound to the alkaline earth metal compound continuously or intermittently. In the case of adding the aliphatic β-diketo compound, the method has the advantage of maintaining the mixture in a powdery state throughout the whole procedure, i.e., from the reaction step to the drying step.

As the manner in which the β-diketo compound is added, there may be mentioned a method which comprises steps of charging a reactor capable of mixing (e.g., apparatuses for kneading or blending powders, such as kneaders, channel-type dryers, ribbon blenders) with the particles or powder of alkaline earth metal hydroxide, and then adding the β-diketo compound continuously or intermittently while stirring the particles or powder.

When adding one component (for example, the alkaline earth metal compound) to the other (for example, the aliphatic β-diketo compound) continuously or intermittently, the proportion of each component at the end of the reaction (the total amount of each component used) need only be within the range set forth.

Since the reaction between the alkaline earth metal compound and the aliphatic β-diketo compound is an exothermic reaction, the reaction is usually performed while controlling the reaction temperature by removing the reaction heat by means of cooling (e.g., jacket cooling). The reaction temperature is, for example, about 0 to 100° C., preferably about 30 to 100° C., more preferably about 60 to 80° C. A reaction temperature exceeding 100° C. causes the loss of the aliphatic β-diketo compound, leading to a consequent reduction in the conversion of the alkaline earth metal compound. As a result, the quality of the resulting β-diketo compound salt (color, purity, stability, etc.) is deteriorated.

In the reaction step, it is preferred that the highest temperature during the reaction is kept at 50° C. or higher (for example, about 50 to 100° C.), 55° C. or higher (for example, about 55 to 95° C., particularly about 55 to 80° C.). When the highest temperature in the reaction is 50° C. or higher, since the conversion rate of the alkaline earth metal compound is raised, the resulting salt of the β-diketo compound is improved in terms of purity and stability.

The reaction may be is carried out in a batch system, a semibatch system or a continuous system.

[Aging]

The reaction mixture obtained batchwise or semi-batchwise may be subjected to an aging if necessary. Aging of the reaction mixture further increases the conversion rate of the alkaline earth metal compound. The temperature for aging is, about 40 to 100° C., preferably about 50 to 90° C., more preferably 60 to 80° C. When the temperature for aging exceeds 100° C., the quality of the resulting β-diketo compound salt (e.g., color, purity, stability) is deteriorated due to the loss of the aliphatic β-diketo compound.

The aging time may suitably be selected. The aging time is usually 1 hour or longer, preferably about 1 to 24 hours (for example, 1 to 16 hours), more preferably about 4 to 12 hours. Alternatively, the time may be about 2 to 8 hours.

[Drying]

The reaction mixture usually contains water of crystallization and water generated during the reaction [for example, 2 mol of by-product water is generated when 1 mol of hydrated lime is used]. Accordingly, the salt of the β-diketo compound is obtained by drying the reaction mixture, directly after the reaction or after completion of the aging, for removing the by-produced water or the water of crystallization.

The drying may be carried out in an atmosphere of an inert gas (for example, nitrogen, helium, carbon dioxide), preferably under a flow (or a stream) of an inert gas (for example, while blowing an inert gas to a reactor). When dried in the air, the product is colored due to the oxidation or condensation of the β-diketo compound. If necessary, the drying operation is performed under reduced pressure.

The drying temperature (when drying while elevating the temperature, this term refers to the finally reached temperature) is usually about 100 to 180° C., preferably about 100 to 150° C. (for example, about 120 to 150° C.). When the drying temperature is lower than 100° C., it is difficult to remove the water of crystallization. Furthermore, insofar as the β-diketo compound salt is not decomposed, the drying temperature can be selected according to the species of the β-diketo compound salt. As to the representative β-diketo compound salts, their preferable drying temperatures are shown in Table 1.

TABLE 1

| Compound | Preferable drying temperature | Decomposition temperature |
| --- | --- | --- |
| Calcium acetylacetonate | 130 to 160° C. | 269° C. |
| Magnesium acetylacetonate | 110 to 120° C. | 160° C. |
| Barium acetylacetonate | 120 to 140° C. | 243° C. |
| Calcium ethyl acetoacetate | 120 to 140° C. | 221° C. |
| Calcium methyl acetoacetate | 120 to 140° C. | 229° C. |
| Magnesium ethyl acetoacetate | 120 to 140° C. | 247° C. |
| Magnesium methyl acetoacetate | 120 to 140° C. | 255° C. |

An excess of the β-diketo compound can be removed by drying. The removed β-diketo compound can be condensed and trapped (or collected) together with the by-produced water using a condenser or the like, and the trapped β-diketo compound is reusable for reactions using other portions of alkaline earth metal compound.

The drying may be performed either in the reactor mentioned above, or in a batch system, a semibatch system or a continuous system.

In the present invention, it is preferred that the powdery alkaline earth metal compound and the β-diketo compound are continuously supplied and dried. The use of an excessive amount of the β-diketo compound relative to the amount of the alkaline earth metal compound and continuous supply of the components make it possible, with industrial advantages, to produce β-diketo compound salts within a short period of time without lowering the quality, and therefore the method of the present invention is economically advantageous. If necessary, the aging operation may be performed.

When the aliphatic β-diketo compound is continuously or intermittently added to the powdery alkaline earth metal compound, for providing a β-diketo compound salt of high quality, it is preferred that 2.1 to 3 mol of the β-diketo compound relative to 1 mol of the alkaline earth metal compound is used; the aging is performed if necessary; and that the resulting salt is dried at 100 to 150° C. in an atmosphere of an inert gas.

The salt of β-diketo compound thus obtained is of high purity, and the purity of which is usually 98.0% by weight or more. Further, the water (moisture) content of the salt is 1% by weight or less, preferably 0.8% by weight or less, more preferably 0.5% by weight or less, and usually about 0.1 to 0.8% by weight (particularly, about 0.1 to 0.5% by weight). Furthermore, the amount of impurities is 2% by weight or less, preferably 1.8% by weight or less, more preferably 1.5% by weight or less, and usually about 0.1 to 1.8% by weight (particularly, about 0.1 to 1.5% by weight). Since the content of impurities is low, the β-diketo compound salt of the present invention is highly stable.

INDUSTRIAL APPLICABILITY

According to the present invention, since the alkaline earth metal content of the β-diketo compound salt is reduced, highly stable β-diketo compound salts of high quality are consequently provided. Further, β-diketo compound salts of high purity can industrially advantageously be produced at high conversions. Furthermore, β-diketo compound salts of high quality can be produced within a short period of time by reacting an alkaline earth metal compound with a β-diketo compound while supplying them continuously, and therefore the method of the present invention is economically advantageous. Thus, the β-diketo compound salt of the present invention can be utilized as a stabilizer for vinyl chloride resins. Particularly, since its moisture content is low, the salt is available for use as a low-effervescent stabilizer. Moreover, the β-diketo compound salt can stably be used over long periods of time due to its high stability.

EXAMPLES

The following examples are intended to describe the present invention in further detail and should by no means be interpreted as defining the scope of the invention.

Comparative Example 1

1,202 g (12.0 mol) of acetylacetone was added to a 3 liter kneader equipped with a thermometer, a dropping funnel, a condenser and a jacket, and then stirred. Then 444 g [6 mol, calcium hydroxide/acetylacetone=1/2.0 (molar ratio)] of calcium hydroxide was added dropwise to the kneader over 3 hours. The reaction temperature was between 32 and 65° C. After completion of the dropping, the mixture was stirred and mixed at a temperature of 65 to 68° C. for 4 hours until the reaction was complete. The resulting product was warmed under a flow of nitrogen gas. At 68° C., the product was subjected to the drying step, and dried at 68 to 73° C. for 24 hours until the product attained a moisture content of 6.8% by weight. The dried product was cooled to give 1,550 g of yellowish white calcium acetylacetonate [yield 99.1 mol % (calcium hydroxide basis), purity 91.5% by weight].

Comparative Example 2

400 g of Calcium acetylacetonate obtained in Comparative Example 1 was dried at 120° C. for 16 hours in a hot air dryer to give 376 g of a powdery substance (moisture 0.6% by weight, purity 97.6% by weight).

Comparative Example 3

444 g (6 mol) of calcium hydroxide was added to the kneader used in Comparative Example 1, and stirred. 1,202 g [12.0 mol, calciumhydroxide/acetylacetone=1/2.0 (molar ratio)] of acetylacetone was added dropwise to the kneader over 6 hours while maintaining the reaction temperature at 40° C. or lower (from 32 to 39° C.). After completion of the dropping, the mixture was further stirred for 40 minutes while ventilating with a nitrogen gas (50 L/hr) until the reaction was complete. The whole product (1683 g) resulted from the reaction was transferred to a rotary evaporator, and dried while ventilating with a nitrogen gas (5 L/hr) at 80° C. for 36 hours under reduced pressure (30 Torr). The moisture content of the product decreased to 6.3–6.4% by weight in 24 hours after the drying operation has started, but little or no change was observed since then. Thereafter, the product was cooled to give 1,540 g of acetylacetone calcium [yield 98.7 mol % (calcium hydroxide basis), moisture 6.3% by weight, purity 91.7% by weight].

Comparative Example 4

While ventilating with a nitrogen gas, 600 g of calcium acetylacetonate obtained in Comparative Example 1 was dried using a rotary evaporator at 120° C. for 8 hours under reduced pressure (30 Torr) to give 563 g of a powder (moisture 0.1% by weight, purity 97.7% by weight).

Example 1

444 g (6 mol) of calcium hydroxide was added to the kneader used in Comparative Example 1, and stirred. Thereafter, 1,320 g [13.2 mol, calcium hydroxide/acetylacetone=1/2.2 (molar ratio)] of acetylaceton was dropped into the kneader over 3 hours. The reaction temperature was between 43 and 65° C. After completion of the dropping, at a temperature of from 65 to 66° C., the mixture was stirred and mixed for aging over 4 hours until the reaction was complete. The resultant powder was slightly moisture-laden. The resulting product was warmed under a flow of nitrogen gas. At the point where the temperature reached 68° C., the product was subjected to the drying step, and dried at 106 to 138° C. for 10 hours until the moisture or water content was reduced to 0.46% by weight. Thereafter, the dried product was cooled to give 1,425 g of white calcium acetylacetonate [yield 98.2 mol % (calcium hydroxide basis), purity 98.6% by weight].

Example 2

350 g (6 mol) of magnesium hydroxide was supplied to the kneader used in Comparative Example 1, and stirred. Thereafter, 1,443 g [14.4 mol, magnesium hydroxide/acetylacetone=1/2.4 (molar ratio)] of acetylacetone was added dropwise into the kneader over 3 hours. The reaction temperature was between 35 and 64° C. After completion of the dropping, at a temperature of 64 to 65° C., the reaction mixture was stirred and mixed for aging for 4 hours until the reaction was complete. The resulting product was warmed under a flow of nitrogen gas. When the temperature was elevated up to 65° C., the product was subjected to the drying step, and dried at 104 to 125° C. for 12 hours until the product attained a moisture content of 0.17% by weight. The dried product was cooled to give 1,342 g of white magnesium acetylacetonate [yield 99.3 mol % (magnesium hydroxide basis), purity 98.9% by weight].

A distillate resulted from the drying was two-layered. 232 g of acetylacetone containing 5.3% by weight of water was collected from the upper layer.

Example 3

444 g (6 mol) of calcium hydroxide was added to the kneader used in Comparative Example 1, and stirred. Thereafter, 1,532 g [13.2 mol, calcium hydroxide/methyl acetoacetate=1/2.2 (molar ratio)] of methyl acetoacetate was added dropwise to the kneader over 3 hours. The reaction temperature was between 36 and 58° C. After completion of the dropping, at a temperature of from 58 to 62° C., the reaction mixture was stirred and mixed for aging for 5 hours until the reaction was complete. The resulting product was warmed under a flow of nitrogen gas. When the temperature reached 62° C., the product was subjected to the drying step, and dried at 110 to 122° C. for 18 hours until the product attained a moisture content of 0.65% by weight. Thereafter, the dried product was cooled to give 1,618 g of white calcium methyl acetoacetate [yield 97.9 mol % (calcium hydroxide basis), purity 98.1% by weight].

Example 4

444 g (6 mol) of calcium hydroxide was added to the kneader used in Comparative Example 1, and stirred. Thereafter, 1,102 g of acetylacetone and 230 g of the acetylacetone collected in Example 2 [total: 1,332 g; 14.4 mol, calcium hydroxide/acetylacetone=1/2.2 (molar ratio)] were added dropwise to the kneader over 3 hours. The reaction temperature was between 46 and 67° C. After completion of the dropping, at a temperature of from 64 to 68° C., the mixture was stirred and mixed for aging for 4 hours until the reaction was complete. The resultant product was warmed under a flow of nitrogen gas. When the temperature was elevated up to 66° C., the product was subjected to the drying step, and dried at 106 to 125° C. for 12 hours until the product attained a moisture content of 0.44% by weight. Thereafter, the dried product was cooled to give 1,435 g of white calcium acetylacetonate [yield 98.5 mol % (calcium hydroxide basis), purity 98.2% by weight].

A distillate resulted from the drying was two-layered. 111 g of acetylacetone containing 5.1% by weight of water was collected from the upper layer.

Example 5

A testing apparatus was fabricated by connecting a 50 L continuous mixing machine for powders (NES-KO-KNEADER), manufactured by Hosokawa Micron Co. Ltd., equipped with metering suppliers for liquids and powders and a jacket with a continuous dryer for powders (solid air dryers) equipped with a vessel, a bag filter and a condenser. Calcium hydroxide and acetylacetone were reacted while supplying them from the metering suppliers to the NES-KO-KNEADER at supplying rates of 3.7 kg/hr (50 mol/hr) and 11.0 kg/hr [110 mol/hr, calcium hydroxide/acetylacetone=1/2.2 (molar ratio)], respectively. The resulting product was continuously supplied to the continuous dryer for powders, and heated with a vapor (158° C.) from the jacket while ventilating with a nitrogen gas (100 L/hr) for continuous drying.

The continuous operation (the reaction temperature of from 81 to 92° C.) as described above was performed for 5 hours to give 59.4 kg of calcium acetylacetonate [yield 98.2 mol % (calciumhydroxide basis), moisture 0.46% by weight, purity 98.6% by weight].

The amount of a distillate from the dryer, which was condensed in the condenser, was 11.7 kg (upper layer 4.8 kg, lower layer 6.9 kg). The upper layer contained 94.9% by weight of acetylacetone and 4.6% by weight of water (or moisture).

Example 6

Using the reactor used in Example 5, calcium hydroxide and acetylacetone was reacted by stirring and mixing while supplying them from the metering suppliers to the NES-KO-KNEADER at supplying rates of 3.7 kg/hr (50 mol/hr) and 14.0 kg/hr [140 mol/hr, calcium hydroxide/acetylacetone=1/2.8 (molar ratio)], respectively. The reaction product was continuously supplied to the continuous dryer for powders, and heated with a vapor (161° C.) from the jacket while ventilating with a nitrogen gas (200 L/hr) for continuous drying.

The continuous operation (the reaction temperature of from 74 to 79° C.) as described above was performed for 5 hours to give 59.7 k of calcium acetylacetonate 9 [yield 99.6 mol % (calcium hydroxidebasis), moisture 0.17% by weight, purity 99.5% by weight].

The amount of a distillate from the dryer, which was condensed in the condenser, was 29.0 kg (upper layer 20.8 kg, lower layer 8.2 kg). The upper layer contained 94.5% by weight of acetylacetone and 5.2% by weight of water (or moisture).

Each calcium acetylacetonate obtained in Example 1, 5, 6, or Comparative Example 1, 2, 3 or 4 was sealed within a container, and kept at a temperature of 25±1° C. under a humidity of 75±2% for examining the stability of the salt. The stability was evaluated from changes in the purity of the acetylacetone as the time went by (from the time of sealing to after 12 months). The results are shown in Table 2.

TABLE 2

|  | Example 1 (purity %) | Example 5 (purity %) | Example 6 (purity %) | Comp. Ex. 1 (purity %) | Comp. Ex. 2 (purity %) | Comp. Ex. 3 (purity %) | Comp. Ex. 4 (purity %) |
| --- | --- | --- | --- | --- | --- | --- | --- |
| Starting time | 98.6 | 98.6 | 99.5 | 91.5 | 97.6 | 91.7 | 97.7 |
| 1 month later | 98.5 | 98.5 | 99.3 | 91.8 | 86.6 | 91.8 | 86.6 |
| 2 months later | 98.8 | 98.8 | 99.6 | 91.1 | 85.9 | 91.1 | 85.9 |
| 3 months later | 98.9 | 98.9 | 99.2 | 90.9 | 85.2 | 90.9 | 85.2 |
| 6 months later | 98.4 | 98.4 | 99.3 | 89.3 | 83.6 | 89.3 | 83.6 |
| 9 months later | 98.7 | 98.7 | 99.1 | 88.2 | 82.4 | 88.2 | 82.4 |
| 12 months later | — | 98.3 | 99.1 | — | — | 84.6 | 80.7 |

As obvious from Table 2, even when the salt is preserved for a long period of time, calcium acetylacetonates obtained in Examples were highly stable, therefore their original purities are almost kept.

Example 7

Using the reactor used in Example 5, calcium hydroxide and methyl acetoacetate were reacted by mixing and stirring while supplying them from the metering suppliers to the NES-KO-KNEADER at supplying rates of 3.7 kg/hr (50 mol/hr) and 13.9 kg/hr [120 mol/hr, calcium hydroxide/methyl acetoacetate=1/2.4 (molar ratio)], respectively. The reaction product was continuously supplied to the continuous dryer for powders, and heated with a vapor (143° C.) from the jacket while ventilating with a nitrogen gas (100 L/hr) for continuous drying.

The continuous operation (the reaction temperature of 82 to 91° C.) as described above was performed for 5 hours to give 67.7 kg of calcium methyl acetoacetate [yield 98.6 mol % (calcium hydroxide basis), moisture 0.61% by weight, purity 98.5% by weight].

The amount of a distillate from the dryer, which was condensed in the condenser, was 18.4 kg (without separation into layers). The distillate contained 62.8% by weight of methyl acetoacetate and 36.6% by weight of water (or moisture).

What is claimed is:

1. A method for producing an alkaline earth metal salt of a β-diketo compound from a powdery alkaline earth metal compound and an aliphatic β-diketo compound, wherein 2.24 mol or more of the aliphatic β-diketo compound is used relative to 1 mol of the alkaline earth metal compound, which comprises carrying out a reaction (1) while supplying the alkaline earth metal compound and the aliphatic β-diketo compound to a reactor in a molar ratio of 1/2.04 to 1/5 (the former/the latter) continuously or intermittently, or (2) by adding the aliphatic β-diketo compound to the powdery alkaline earth metal compound continuously or intermittently, and drying the resulting product in an atmosphere of an inert gas at a temperature of 100 to 180° C., wherein the total amount of the aliphatic β-diketo compound is from 2.2 to 3 mol relative to 1 mol of the powdery alkaline earth metal compound.

2. The method according to claim 1, wherein the highest temperature during the reaction between the alkaline earth metal compound and the aliphatic β-diketo compound is 50° C. or higher.

3. The method according to claim 1, wherein the reaction mixture is aged.

4. The method according to claim 1, wherein the alkaline earth metal compound is calcium hydroxide, magnesium hydroxide or barium hydroxide.

5. The method according to claim 1, wherein the aliphatic β-diketo compound is represented by the following formula (1):

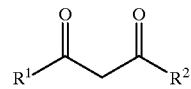

(1)

wherein $R^1$ and $R^2$ are same or different, each representing a hydrogen atom, a $C_{1-6}$ alkyl group, or a $C_{1-10}$ alkoxy group.

6. The method according to claim 1, wherein the aliphatic β-diketo compound is an acetoacetic acid $C_{1-4}$ ester or acetylacetone.

7. The method according to claim 1, which comprises adding the aliphatic β-diketo compound to the powdery alkaline earth metal compound continuously or intermittently, and drying the resulting product in an atmosphere of an inert gas at a temperature of 100 to 150° C.

8. The method according to claim 1 wherein the resultant alkaline earth metal salt of a β-diketo compound has a moisture content of 1% by weight or less, and a purity of 98.0% by weight or higher.

* * * * *

UNITED STATES PATENT AND TRADEMARK OFFICE
CERTIFICATE OF CORRECTION

PATENT NO.   : 6,376,719 B1
DATED        : April 23, 2002
INVENTOR(S)  : Masayuki Okada It is certified that error appears in the above-identified patent and that said Letters Patent is hereby corrected as shown below:

Column 10,
Line 4, change "2.24 mol" to -- 2.2 mol --.
Line 9, change "1/2.04" to -- 1/2.2 --.

Signed and Sealed this

Fifth Day of November, 2002

Attest:

Attesting Officer

JAMES E. ROGAN
Director of the United States Patent and Trademark Office